United States Patent [19]

Barron et al.

[11] Patent Number: 5,972,903
[45] Date of Patent: Oct. 26, 1999

[54] METHOD FOR PROMOTING ANGIOGENESIS USING HEPARIN AND ADENOSINE

[75] Inventors: Hal V. Barron, San Francisco; Elias Botvinick, San Rafael, both of Calif.

[73] Assignee: Regents of the University of California Corporation, Oakland, Calif.

[21] Appl. No.: 08/946,196

[22] Filed: Oct. 7, 1997

[51] Int. Cl.$^6$ .......................... A61K 31/70; A61K 31/725; C08L 5/10
[52] U.S. Cl. ................................. 514/46; 514/56; 514/824
[58] Field of Search ................................ 514/46, 56, 824

[56] References Cited

U.S. PATENT DOCUMENTS

| | | |
|---|---|---|
| 3,819,612 | 6/1974 | Imai et al. . |
| 3,819,613 | 6/1974 | Marumoto et al. . |
| 4,738,954 | 4/1988 | Hamilton et al. . |
| 4,868,160 | 9/1989 | Hamilton et al. . |
| 4,886,786 | 12/1989 | Lindstrom et al. . |
| 4,954,504 | 9/1990 | Chen et al. . |
| 5,034,381 | 7/1991 | Hutchison et al. . |
| 5,063,233 | 11/1991 | Chen et al. . |
| 5,104,859 | 4/1992 | Sollevi . |
| 5,140,015 | 8/1992 | Olsson et al. . |
| 5,231,086 | 7/1993 | Sollevi . |
| 5,236,908 | 8/1993 | Gruber et al. ............................ 514/46 |
| 5,275,812 | 1/1994 | Gold et al. . |
| 5,278,150 | 1/1994 | Olsson et al. . |
| 5,449,665 | 9/1995 | Sollevi . |
| 5,462,752 | 10/1995 | Chao et al. . |
| 5,529,986 | 6/1996 | Larsson et al. . |
| 5,534,504 | 7/1996 | Sollevi . |
| 5,593,688 | 1/1997 | Baldeschwieier . |
| 5,593,875 | 1/1997 | Wurm et al. . |
| 5,731,296 | 3/1998 | Sollevi . |

FOREIGN PATENT DOCUMENTS

| | | |
|---|---|---|
| 96 12496 | 5/1996 | WIPO . |
| 96 13158 | 5/1996 | WIPO . |
| 96 18293 | 6/1996 | WIPO . |

OTHER PUBLICATIONS

Bautovich, G., et a., "Detection of Deep Venous Thrombi and Pulmonary Embolus with Technetium–99m–DD–3B6/22 Anti–fibrin Monoclonal Antibody Fab' Fragment," *J. Nucl. Med.* vol. 35, pp. 195–202 (1994).

Buckley and Sorkin, "Enoxaparin: A review of its pharmacology and clinical applications in the prevention and treatment of thromboembolic disorders," *Drugs*, vol. 44, pp. 465–497 (1992).

Japanese Abstract: JP01 187083 Nippon Mining Co. LTD, Jul. 1989.

Chan, Sammy Y., "Comparison of Maximal Myocardial Blood Flow During Adenosine Infusion With That of Intravenous Dipyridamole in Normal Men," *JACC*, vol. 20, No. 4, pp. 979–985 (1992).

Chiarugi, V., "Cooperation of Heparin With Other Angiogenetic Effectors," *International Journal of Tissue Reactions*, VII(2), pp. 129–133 (1986).

Faulds, Diana, "Adenosine An Evaluation of its Use in Cardiac Diagnostic Procedures, and in the Treatment of Paroxysmal Supraventricular Tachycardia," *Drugs*, pp. 596–624 (1991).

Hara, Toshihiko, "Quantitative measurement of regional myocardial blood flow in patients with coronary artery disease by intravenous injection of $^{13}$N–ammonia in positron emission tomography," *Nuclear Medicine*, pp. 231–235 (1990).

Hutchins, Gary D., "Positron Emission Tomography to Quantitate Myocardial Perfusion," *American Journal of Cardiac Imaging*, vol. 7, No. 4, pp. 283–293 (1993).

Hutchins, Gary D., "Noninvasive Quantification of Regional Blood Flow in the Human Heart Using N–13 Ammonia and Dynamic Positron Emission Tomographic Imaging," *JACC*, vol. 15, No. 5, pp. 1032–1042 (1990).

Luria, Myron H., "Cardiovascular Risk Factor Clustering and Ratio of Total Cholesterol to High–Density Lipoprotein Cholesterol in Angiographically Documented Coronary Artery Disease," *American Journal of Cardiology*, vol. 67, pp. 31–36 (1991).

McAuslan, B.R., "Angiogenic Factors and Their Assay: Activity of Formyl Methionyl Leucyl Phenylalanine, Adenosine Diphosphate, Heparin, Copper, and Bovine Endothelium Stimulating Factor," *Microvascular Research*, pp. 323–338 (1983).

Schelbert, M.D., Heinrich R., "Consideration of Measurements of Myocardial Blood Flow with Positron–Emission Tomography," *Investigative Radiology*, vol. 28, Supp. 4, pp. S47–S55 (1993).

Soufer, M.D., Robert, et al., "Positron Emission Tomography And the Quantitative Assessment of Regional Myocardial Blood Flow," *JACC*, vol. 15, No. 1, pp. 128–130 (1990).

Symons, J. David, "Repeated Dipyridamole Administration Enhances Collateral–Dependent Flow and Regional Function During Exercise," *Department of Internal Medicine*, pp. 503–513 (1992).

Terrell, Grace E., "Indirect Angiogenic Agents Do Not Release Fibroblast Growth Factors From Extracellular Matrix," *Matrix*, vol. 11, pp. 108–114 (1991).

Tucker, K.J., "The applications of adenosine in noninvasive cardiac imaging," *Herz* 17, pp. 122–136 (1992).

(List continued on next page.)

*Primary Examiner*—Gary L. Kunz
*Attorney, Agent, or Firm*—Burns, Doane, Swecker & Mathis, L.L.P.

[57] ABSTRACT

This invention relates to a method of promoting growth of new blood vessels, i.e., angiogenesis, by coadministration of an adenosine receptor agonist, e.g., adenosine, and heparin over a period of several days. In particular, this invention is applicable to promoting angiogenesis to improve collateral coronary circulation in patients suffering from myocardial infarction.

8 Claims, No Drawings

OTHER PUBLICATIONS

Unger, Ellis F., "Heparin promotes the formation of extracardiac to coronary anastomoses in a canine model," *American Journal of Physiology,* vol. 260, No. 5, pp. H1625–H1634 (1991).

Valk, P.E., "Quantitative Assessment of Reversible Myocardial Ischemia by Dipyridamole Perfusion," *The Journal of Nuclear Medicine,* vol. 30, No. 5, pp. 760 (1989).

Araie, E. et al., "Heparin exercise treatment following percutaneous transluminal coronary angioplasty in a patient with effort angina," *Heart and Vessels,* vol. 6, pp. 181–183 (1991).

Ely, S.W. et al., "Protective effects of adensoine in myocardial ischemia," *Circulation,* vol. 85, No. 3, pp. 893–904 (1992).

Ethier, M.F. et al., "Adenosine stimulates proliferation of human endothelial cells in culture," *Am. J. Physiol.,* pp. H131–H138, (1993).

Fujita, M. et al., "Longterm efficacy of heparin exercise treatment for patients with chronic effort angina; evaluation by exercise T1–201 myocardial scintigraphy," *Int. J. Cardiol.,* vol. 40, pp. 51–56, (1993).

Fujita, M. et a., "Comparative effect of heparin treatment with and without strenuous exercise on treadmill capacity in patients with stable effort angina," *Am. Heart Journal.,* vol. 122, pp. 453–457, (1991).

Melandri, G. et al., "Benefit of adding low molecular weight heparin to the conventional treatment of stable angina pectoris. A double–bloind, randomized,placebo–controlled trial," *Circulation,* vol. 88, pp. 2517–2523, (1993).

Norrby, K. et al., "Heparin enhances angiogenesis by a systemic mode of action," *Int. J. Exp. Pathol.* vol. 73, pp. 147–155, (1992).

Sasayama, S. et al., "Recent insights into coronary collateral circulation," *Circulation,* vol. 85, pp. 1197–1204, (1992).

Quyyumi, A. A. et al., "Angiogenic effects of low molecular weight heparin in patients with stable coronary artery disease: a pilot study." *J. Am. Coll. Cardiol.,* vol. 22, No. 3, pp. 635–641, (1992).

Norrby et al. Int. J. Exp. Physiol. 73:147, 1992.

Ethièr. et al. Am. J. Physiol. H131, 1993.

METHOD FOR PROMOTING ANGIOGENESIS USING HEPARIN AND ADENOSINE

FIELD OF THE INVENTION

The present invention relates to a method for promoting the growth of new blood vessels (angiogenesis) especially coronary blood vessels after myocardial infarction.

BACKGROUND OF THE INVENTION

It is estimated that five million people are afflicted with chronic stable angina in the United States. Each year 200,000 people under the age of 65 die with what is termed "premature ischemic heart disease." Despite medical therapy, many go on to suffer myocardial infarction and debilitating symptoms prompting the need for revascularization with either percutaneous transluminal coronary angioplasty or coronary artery bypass surgery. Medical researchers have postulated that one way of relieving myocardial ischemia would be to enhance coronary collateral circulation.

Fujita et. al. (1,2) demonstrated that heparin in combination with short term exercise training improved exercise tolerance as measured by dynamic exercise testing. The researchers, believing this effect was mediated through increased collateral vascular development, examined the effects of heparin in combination with a brief concomitant exercise training protocol on coronary collateral flow. Thallium-201 myocardial perfusion images obtained in association with the same work-load both before and late after combined heparin exercise treatment, which indicated that coronary collateral circulation was enhanced. Such dramatic changes over a short term do not occur naturally, and suggest that angiogenesis has taken place. These investigators carried out further studies which demonstrated that exercise alone or heparin alone were insufficient stimuli for collateral development (1). That is, only when exercise and heparin were combined were they able to elicit this apparent angiogenic response. Other studies suggests that exercise induce ischemia combined with heparin increases coronary collateral flow.

More recently Quyyumi et. al. (4) studied the anti-ischemic effects of combined treatment with low molecular weight heparin and exercise induced ischemia. Twenty three patients received either heparin or placebo in combination with an exercise protocol for 4 weeks. Eighty percent of the low molecular weight heparin (LMWH) group compared with 31% of placebo group had a significant increase in rate-pressure product at the onset of 1 mm of ST segment depression. Further the time to ischemia increased in 100% of the LMWH group compared with 62% in the placebo group. In this same population the incidence and duration of ST segment depression during ambulatory holter monitor decreased by 30 and 35% respectively compared with 0% in controls.

These authors concluded that exercise and LMWH lessens myocardial ischemia and that the improvement is likely to be mediated by enhanced collateral function. Similar findings resulted from another double-blind, randomized, placebo-controlled trial, involving 29 patients with stable exercise-induced angina pectoris who received a single daily subcutaneous injection of LMWH Parnaparin (trademark for a brand of heparin)

Correlations have now been made between the anatomic appearance of coronary collateral vessels ("collaterals") visualized at the time of intracoronary thrombolitic therapy during the acute phase of myocardial infarction and the creatine kinase time-activity curve, infarct size, and aneurysm formation. These studies demonstrate a protective role of collaterals in hearts with coronary obstructive disease, showing smaller infarcts, less aneurysm formation, and improved ventricular function compared with patients in whom collaterals were not visualized.

When the cardiac myocyte is rendered ischemic, collaterals develop actively by growth with DNA replication and mitosis of endothelial and smooth muscle cells. One hypothesis suggest that heparin-binding growth factors are present in the heart, or biological activity is quiescent under normal physiological conditions. Once ischemia develops, these factors are activated and become available for receptor occupation, which may initiate angiogenesis after exposure to exogenous heparin. Unfortunately, the "natural" process by which angiogenesis occurs is inadequate to reverse the ischemia in almost all patients with coronary artery disease.

The etiology of the benefit of combined heparin-exercise treatment is unknown with certainty (6,7). One possibility is that ischemia stimulates the release or expression of some angiogenic substance which in combination with heparin stimulates collateral development. During ischemia adenosine is released through the breakdown of ATP. Many cardioprotective roles have been discovered for adenosine including hemodynamic changes such as bradycardia and vasodilatation and adenosine has been suggested to have a role in such unrelated phenomena as preconditioning and possibly the reduction in reperfusion injury(8).

Intrinsic adenosine may facilitate the coronary flow response to increased myocardial oxygen demands and so modulate the coronary flow reserve. Ethier et. al. (9) demonstrated that the addition of physiological concentrations of adenosine to human umbilical vein endothelial cell cultures stimulates proliferation, possibly via a surface receptor. They suggested that adenosine may be a factor for human endothelial cell growth and possibly angiogenesis. Angiogenesis appears to be protective for patients with CAD, but the rate at which blood vessels grow naturally is inadequate to reverse their disease. Thus, strategies to enhance and accelerate the body's natural angiogenesis potential should be beneficial in patients with CAD.

REFERENCES (1) Fujita, M.; Yamanishi, K.; Hirai, T.; Ohno, A.; Sasayame, S., "Comparative effect of heparin treatment with and without strenuous exercise on treadmill capacity in patients with stable effort angina," Am. Heart Journal., 1991; 122:453.

(2) Fujita, M.; Ohn, A.; Miwa, K.; Sasayama, S.; Futatsuya, R.; Seto, H., "Longterm efficacy of heparin exercise treatment for patients with chronic effort angina; evaluation by exercise T1-201 myocardial scintigraphy," Int J. Cardiol., 1993; 40:51.

(3) Araie, E.; Fujita, M.; Miwa, K.; Miyagi, K.; Sasayama, S., "Heparin exercise treatment following percutaneous transluminal coronary angioplasty in a patient with effort angina," Heart Vessels, 1991; 6: 181.

(4) Quyyumi, A. A.; Diodati, J. G.; Lakatos, E.; Bonow, R. O.; Epstein, S. E. "Angiogenic effects of low molecular weight heparin in patients with stable coronary artery disease: a pilot study." J. Am. Coll. Cardiol., 1993; 22:635.

(5) Melandri, G.; Semprini, F.; Cervi, V.; Candiotti, N,; Palazzini, E.; Branzi, "Benefit of adding low molecular weight heparin to the conventional treatment of stable angina pectoris. A double-bloind, randomized,placebo-controlled trial," Circulation, 1993; 88: 2517.

(6) Norrby, K.: Sorbo, J., "Heparin enhances angiogenesis by a systemic mode of action," Int J. Exp. Pathol. 1992; 73: 147.

(7) Sasayama, S.; Fujita, M., "Recent insights into coronary collateral circulation," Circulation, 1992; 85: 1197.

(8) Ely, S. W.; Berne, R. M., "Protective effects of adensoine in myocardial ischemia," Circulation, 1992; 85: 893.

(9) Ethier, M. F.; Chander, V.; Dobson, J. J., "Adenosine stimulates proliferation of human endothelial cells in culture," Am. J. Physiol., 1993; H131.

There is a need for an effective therapy for promotion of coronary angiogenesis with minimum side effects. Such a therapy would be particularly useful for patients who have myocardial infarctions and could be used prophylactically in patients who have poor coronary circulation are placing them at high risk of ischemia and myocardial infarctions.

SUMMARY OF THE INVENTION

One aspect of the present invention is a method of promoting angiogenesis in a patent in need thereof comprising coadministration of an exogenous adenosine receptor agonist and heparin in low, daily dosage for a week or more. The method of the present invention may be used as a treatment to restore cardiac function after a myocardical infaction improve blood flow in patients with coronary artery disease suffering from myocardial ischemia or inadequate blood flow to areas other than the heart such as in peripheral vascular disease, where decreased blood flow is a problem.

A second aspect of the present invention is a sterile, injectable, pharmaceutical formulation comprising a angiogenically effective amount of heparin and an adenosine receptor agonist in a physiologically and pharmaceutically acceptable carrier, optionally with one or more excipients.

DETAILED DESCRIPTION OF THE INVENTION

As used herein the terms "regeneration of blood vessels," "angiogenesis," "revascularization," and "increased collateral circulation" (or words to that effect) are considered as synonymous. The term "pharmaceutically acceptable" when referring to a natural or synthetic substance means that the substance has an acceptable toxic effect in view of its much greater beneficial effect, while the related the term, "physiologically acceptable," means the substance has relatively low toxicity. The term, "coadministered" means two or more drugs are given to a patient at approximately the same time or in close sequence so that their effects run approximately concurrently or substantially overlap. This term includes sequential as well as simultaneous drug administration.

The amounts of an adenosine receptor agonist and heparin required to be effective in stimulating angiogenesis will, of course, vary with the individual being treated and is ultimately at the discretion of the physician. The factors to be considered include the condition of the patient being treated, the efficacy of the particular adenosine receptor agonist being used, the nature of the formulation, and the patient's body weight. However, a suitable angiogenic does of heparin and an adenosine receptor agonist is in the range of about 5000 to about 10,000 U/d heparin and about 40 mg to about 80 mg of an adenosine receptor agonist for ten days. While it possible to administer heparin and an adenosine receptor agonist simultaneously, preferably heparin is given as a bolus about twenty minutes before starting the infusion of the adenosine receptor agonist.

Typically, heparin is infused as a bolus of about 15,000 U about 15 minutes prior to the adenosine receptor agonist administration. The adenosine receptor agonist, e.g. adenosine, is then infused for about 5 to about 8 minutes at a rate of about 140 $\mu$g/Kg/min (based on body weight). Thus, a total dose for a 80 Kg patient is about 67 mg. This dosage regiment is repeated daily for about 10 days. The adenosine receptor agonist-heparin infusions can be used to stimulate angiogenesis in patients with symptomatic coronary artery disease in place of other more invasive and expensive therapies such as angioplasty or even coronary artery bypass grafting surgery (CABG).

Currently the most widely used adenosine receptor agonist is adenosine, per se. Other adenosine receptor agonist include those taught in U.S. Pat. Nos. 3,819,612, 3,819,613, 4,954,504, 5,034,381, 5,063,233, 5,140,015, 5,278,150, and 5,593,875 all of which are incorporated herein by reference. Because adenosine receptors are found throughout the human body, increased stimulation of these receptors can have profound, and often detrimental, physiological, effects on organs through out the body which limits the amount of an adenosine receptor agonist. Therefore, selective adenosine receptor agonists are preferred.

While the adenosine receptor agonist can be administered to a patient in any pharmacologically and pharmaceutically acceptable form for use in continuous, intravenous infusion, it is preferable for the adenosine receptor agonist to be administered in an isotonic, aqueous solution. In the method of the present invention, both heparin and the adenosine receptor agonist are administered in sterile, buffered, dilute aqueous solutions. Preferably, excipient such as preservatives, stabilizers, and antioxidants are added to these solution to enhance their properties. The prototypical adenosine receptor agonist, adenosine, per se, of sufficient quality for use with the present invention can be obtained from several sources, e.g., from Fujisawa under the trademark AdenoscanO. Likewise, pharmaceutical forms of heparin, usually a sodium heparin are also readily available.

Treatment of a human by slow infusion of an adenosine receptor agonist over a period of several days but without heparin promotes angiogenesis to some degree. However, to maximize angiogenesis, preferably the adenosine receptor agonist is administered in conjunction with heparin.

EXAMPLES

The following examples illustrate aspects of the present invention but should not be construed as limitations. The symbols and convention used in these examples are consistent with those used in contemporary medical and scientific literature.

Example 1
Evaluation of the Present Invention

To evaluated the present invention, patients in need of coronary angiogenesis are randomized to receive either adenosine/heparin or control saline infusion. Infusions occurs daily for about 10 days and are given in the morning to the patients who have fasted overnight. Infusion is through an IV line. A heparin lock intravenous line is placed on day one of the study and is left in place for 72 hours. After the 72 hour period, another heparin lock is replaced. Heparin is infused as a bolus of 10,000 U and about 15 minutes prior to the adenosine administration.

With the patient in the supine position, intravenous adenosine is infused for about 6 minutes at a rate of 140 $\mu$g/kg/min (based on actual body weight) for a total dose of 0.84 μg/kg. A suitable injectable formulation of adenosine is available under the trade mark Adenoscan® (Fujisawa). A 12-lead ECG, blood pressure measurements and heart rates is recorded at baseline, at 1-minute intervals during the infusion of adenosine and during recovery. If a patient fails to tolerate the full 6 minutes the test is terminated. The infusion is terminated if severe hypotension (systolic blood pressure <90 mmHg) or ischemia (>2 nun horizontal ST segment depression below baseline). After the infusion the patients are observed for a full three hours to determine whether there are any late side-effects.

Infusion may be carried out by substantially any techniques customary in the art of medical practice. However, the plasma half-life of adenosine is quite short, and adenosine is active at very low dosage. Therefore, fluctuations in serum levels of adenosine should be minimized through the use of a calibrated infusion pump.

All patients are observed for adverse effects for three hours following each drug infusion and again at 24 hours. Any reactions such as flushing, lightheadedness, nonischemic chest pain, nausea, headache, and shortness of breath are noted, and any treatment employed are recorded.

Example 2

The Myocardial Perfusion Studies

In the pre-study phase, an exercise-augmented thallium TI-20 myocardial perfusion scan is preformed and is repeated upon completion of the 10 day protocol.

The exercise-augmented thallium TI-201 myocardial perfusion scans are processed by conventional software to ensure a uniform appearance. The scintigrams are then evaluated by blinded experienced readers. Both fixed and reversible defects are quantified using polar coordinate maps and correlated with an objective conventional 16 segment model of the myocardium.

For each set of scintigrams the reader is blindly evaluating the early images to the late images and assessing the degree of change in reversible ischemic myocardium. Objective evaluation of defects are made as are analyses of polar coordinate plot with comparison to a normal data base.

Example 3

Injectable Formulation of Adenosine

The active ingredient and buffering agents are dissolved in propylene glycol at about 55° C. The water for injection is then added with stirring and the resulting solution is filtered, filled into an ampule and the ampule is sealed and sterilized by autoclaving.

| Ingredients | Amount |
| --- | --- |
| Active ingredient (Adenosine) | 3.0 mg |
| Porpylene glycol | 0.4 mL |
| Water for injection* | q.s. 1 mL |

*The term "water for injection" means sterile, purified water containing electrolytes such as sodium chloride and buffering agents so that it is compatible to human physiological fluids such as blood.

Example 4

Injectable Formulation of Adenosine and Heparin

The active ingredient and buffering agents are dissolved in propylene glycol at about 55° C. The water for injection is then added with stirring and the resulting solution is filtered, filled into an ampule and the ampule is sealed and sterilized by autoclaving.

| Ingredients | Amount |
| --- | --- |
| Active ingrdient (Adenosine) | 3 mg |
| (Heparin) | 10,000 U |
| Propylene glycol | 0.4 mL |
| Water for injection | q.s. 1 mL |

What is claimed is:

1. A method of promoting coranary angiogenesis in a patient in need thereof comprising coadministration of an adenosine and heparin in daily dosages for a week or more, wherein the adenosine is administered via intravenous injection.

2. The method of claim 1 wherein the adenosine is in the dosage range of about 40 mg/kg to about 80 mg/kg and the heparin is in the dosage range of about 5,000 U to about 10,000 U coadministered continuously intravenously for about six minutes a day for a week or more.

3. The method of claim 1 wherein the heparin is administered as a bolus injection prior to administering the adenosine.

4. The method of claim 1 wherein heparin is administered as a bolus injection of about 50,000 to about 100,000 units, about ten to about twenty minutes prior administering the adenosine by infusion at a rate of about 100 μg/kg/min to about 200 μg/kg/min for about 5 to about 10 minutes every day.

5. The method of claim 4 wherein heparin is administered as a bolus injection of about 10,000 U, about fifteen minutes prior administering the adenosine by infusion at a rate of about 140 μg/kg/min for about six minutes each day for about ten days.

6. A pharmaceutical formulation for injection into a patient comprising adenosine and heparin in a sterile, aqueous, pharmaceutical formulation.

7. The pharmaceutical formulation of claim 6 wherein the concentration of adenosine is about 40 mg to about 80 mg and the concentration of heparin is about 5,000U to about 100,000 U.

8. The pharmaceutical formulation of claim 6 additionally comprising one or more pharmaceutically acceptable excipients.

* * * * *

UNITED STATES PATENT AND TRADEMARK OFFICE
CERTIFICATE OF CORRECTION

PATENT NO. : 5,972,903            Page 1 of 2
DATED : October 26, 1999
INVENTOR(S) : Hal V. Barron and Elias Botvinick It is certified that error appears in the above-identified patent and that said Letters Patent is hereby corrected as shown below:

| Location | Delete | Insert |
|---|---|---|
| References, page 2, Melandri | "double-bloind" | --double-blind-- |
| References, page 2, Ely | "adensoine" | --adenosine-- |
| Column 1, line 30 | "images obtained" | --images were obtained-- |
| Column 1, line 40 | "induce ischemia" | --induced ischemia-- |
| Column 1, line 43 | "et. al." | --et al.-- |
| Column 1, line 45 | "Twenty three" | --Twenty-three-- |
| Column 2, line 32 | "et. al." | --et al.-- |
| Column 2, line 66 | "double-bloind" | --double-blind-- |
| Column 3, line 7 | "adensoine" | --adenosine-- |
| Column 3, line 16 | "circulation are" | --circulation that is-- |
| Column 3, line 26 | "infaction" | --infarction, to-- |
| Column 3, line 40 | "angiogenesis"" | --"angiogenesis"-- |
| Column 3, line 46 | "related the term" | --related term-- |
| Column 3, line 60 | "does" | --dose-- |
| Column 4, line 7 | "regiment" | --regimen-- |
| Column 4, line 14 | "agonist" | --agonists-- |

UNITED STATES PATENT AND TRADEMARK OFFICE
CERTIFICATE OF CORRECTION

PATENT NO. : 5,972,903  Page 2 of 2
DATED      : October 26, 1999
INVENTOR(S): Hal V. Barron and Elias Botvinick It is certified that error appears in the above-identified patent and that said Letters Patent is hereby corrected as shown below:

| | | |
|---|---|---|
| Column 4, line 21 | "through out" | --throughout-- |
| Column 4, line 31 | "excipient" | --excipients-- |
| Column 4, line 33 | "solution" | --solutions-- |
| Column 4, line 37 | " adenoscan0" | --Adenoscan®-- |
| Column 4, line 55 | "evaluated" | --evaluate-- |
| Column 5, line 4  | "is recorded" | --are recorded-- |
| Column 5, line 27 | "preformed" | --performed-- |
| Column 5, line 39 | "evaluation" | --evaluations-- |
| Column 6, line 20 | "coranary" | --coronary-- |
| Column 6, line 35 | "prior administering" | --prior to administering-- |
| Column 6, line 43 | "prior administering" | --prior to administering-- |

Signed and Sealed this

Sixteenth Day of January, 2001

Attest:

Q. TODD DICKINSON

Attesting Officer     Commissioner of Patents and Trademarks